US00PP23081P2

(12) United States Plant Patent
Lichacz

(10) Patent No.: US PP23,081 P2
(45) Date of Patent: Sep. 25, 2012

(54) ***HOSTA* PLANT NAMED 'GOODNESS GRACIOUS'**

(50) Latin Name: ***Hosta* hybrid**
Varietal Denomination: Goodness Gracious

(75) Inventor: Susan Lichacz, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 23 days.

(21) Appl. No.: 13/065,969

(22) Filed: Apr. 4, 2011

(51) Int. Cl.
*A01H 5/00* (2006.01)

(52) U.S. Cl. ..... Plt./353

(58) Field of Classification Search ..... Plt./353
See application file for complete search history.

*Primary Examiner* — Susan McCormick Ewoldt

(57) ABSTRACT

*Hosta* plant named 'Goodness Gracious' is a new cultivar with ovate leaves with wide yellow margins and dark green centers, light lavender flowers suitable as a potted plant, for the garden, and for cut flower or leaf arrangements.

1 Drawing Sheet

Botanical classification: *Hosta* hybrid (Tratt.).
Variety denomination: 'Goodness Gracious'.

BACKGROUND OF THE INVENTION

The present invention relates to the new and distinct *Hosta* plant, *Hosta* 'Goodness Gracious' discovered by Susan Lichacz at a nursery in Zeeland, Mich., USA as an uninduced whole plant mutation in a tissue cultured crop of *Hosta* 'Satisfaction' (not patented). The new plant has been successfully asexually propagated both by division and by tissue culture at a nursery in Zeeland, Mich. and in both asexual propagation systems found to be stable and produce identical plants that maintain the unique characteristics of the original plant.

BRIEF SUMMARY OF THE INVENTION

*Hosta* 'Goodness Gracious' differs from its parent, 'Satisfaction', as well as all other *Hostas* known to the applicant. The most similar known *Hosta* cultivars are: 'Evening Magic' (not patented), 'Everglades' (not patented), 'Lakeside Symphony' (not patented), 'Moonshine' (not patented), 'Piedmont Special' (not patented), 'Satisfaction' (not patented), 'Sentimental Journey' (not patented), 'Summer Serenade' (not patented), and 'Tylers' Treasure' (not patented). All of the above are sports (mutations) of 'Piedmont Gold' (not patented). *Hosta* 'Evening Magic' has leaves with a yellow center and thin white margin. *Hosta* 'Moonshine' has solid chartreuse foliage. *Hosta* 'Lakeside Symphony' has a muted chartreuse leaf margin with a yellow center. *Hosta* 'Sentimental Journey' has leaves with a light green center and yellow margin. *Hosta* 'Summer Serenade' has foliage with a yellow center and dark green margin, the reverse pattern of 'Goodness Gracious'. *Hosta* 'Goodness Gracious' has color pattern similar to 'Everglades', 'Piedmont Special', 'Satisfaction' and 'Tyler's Treasure' but with a much wider variegation of the leaf margins.

There are over 4,500 cultivars registered with The American *Hosta* Society, which is the International Cultivar Registration Authority for the genus *Hosta*. *Hosta* 'Goodness Gracious' differs from these and all unregistered cultivars known to the inventor in the following combined traits:

1. Plant size of medium-large with arching foliage.
2. Foliage with coarse marginal undulation or pie-crusting to leaf blade.
3. Leaf blades with narrow dark green centers and very wide lutescent margins.
4. Numerous flowers of light lavender to near white on upright scapes attractively above foliage in early summer.

BRIEF DESCRIPTION OF THE DRAWINGS

The photographs of the three-year old plant demonstrate the overall appearance of the near-mature plant, including the unique traits, grown in a partially shaded garden in Zeeland, Mich. The colors are as accurate as reasonably possible with color reproductions. Ambient light spectrum, source, direction and temperature may cause the appearance of minor variation in color.

DETAILED BOTANICAL DESCRIPTION

Figure 1:
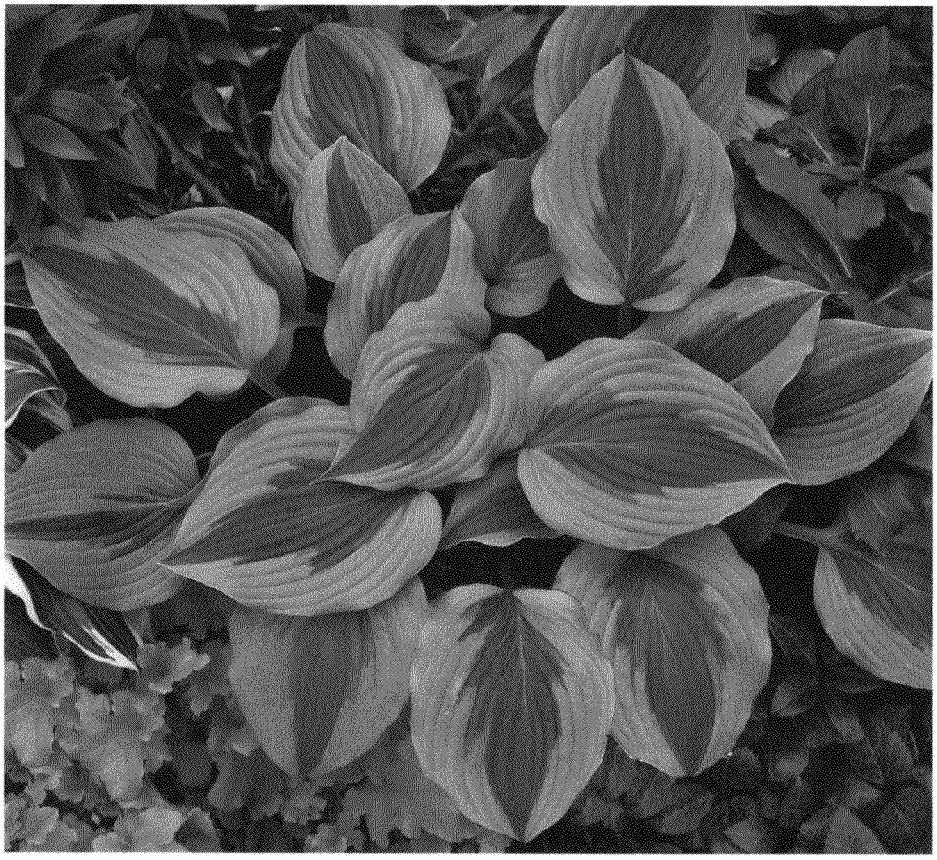
FIG. 1 shows the new plant in a landscape setting early in the growing season.
Figure 2:
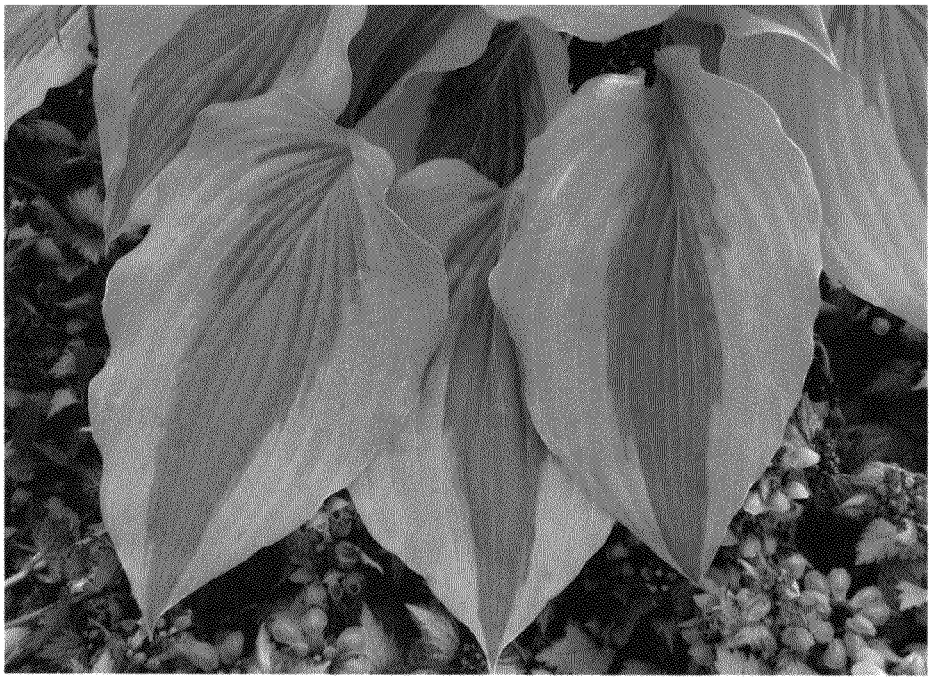
FIG. 2 shows a close-up of the foliage later in the season.

The following descriptions and color references are based on the 2001 edition of The Royal Horticultural Society Colour Chart except where common dictionary terms are used. The new plant, *Hosta* 'Goodness Gracious', has not been observed under all possible environments. The phenotype may vary slightly with different environmental conditions, such as temperature, light, fertility, moisture and specimen maturity, but without any change in the genotype. The following observations and size descriptions are of a three-year old plant in a trial garden in Zeeland, Mich. with 50% artificial shade, supplemental water and light fertilizer.

Botanical classification: *Hosta* hybrid.
Sport parentage: *Hosta* 'Satisfaction' (not patented).
Propagation method: By sterile laboratory tissue culture propagation and garden division.
Growth rate: Moderate to rapid.
Crop time: Summer growing 9 to 10 weeks to finish in a one-liter container.

Time to initiate roots from tissue culture: About two and a half weeks.

Plant description:

*Plant shape and habit*.—Hardy, herbaceous, long-lived perennial, densely rhizomatous, forming a mounded clump in maturity, with basal rosette leaves, usually bilateral and radially symmetrical.

*Roots*.—Normal, fleshy, lightly branching, cream-colored in normal soil.

*Plant size*.—Foliage height about 50 cm tall; width of plant at the widest point is approximately 48 cm at the widest point just above soil line.

Foliage description:

*Leaf blade*.—Ovate, entire margins, cordate leaf base with narrowly acute apex, mostly bilaterally symmetrical, with sinuous or pie-crust margins, with deeply impressed veins; width to length ratio of about 1:1.3; average about 22 cm long and 17 cm wide; 10 to 11 pairs of major parallel veins and one main center vein; glabrous; top surface begins season lightly glaucous becoming dull matte-surfaced to slightly shiny, bottom surface glaucous; margin variegation portion increasing with age to nearly ½ total leaf width.

*Blade color*.—Very early season as emerging adaxial (top) center between RHS 138A and RHS 138B, adaxial margin nearest RHS144A; very early season as emerging abaxial (bottom) center nearest RHS 138B, abaxial margin nearest RHS 138C; early season adaxial center nearest RHS 137A, adaxial margin nearest RHS N144C with irregular segments between the margin and center where the histogenic layers overlap of RHS 144A and RHS 144B; early season abaxial (underside) center nearest RHS 138A, adaxial margin RHS 144A with some small fragments connected to center of nearest RHS138B between margin and center where histogenic layers overlap; mid-season and later adaxial center nearest RHS 137A and margin more yellow than RHS 151D; mid-season and later abaxial center nearest RHS 138A and margins more yellow than RHS 151D.

*Veins*.—10 to 11 pairs of prominent major parallel veins, deeply impressed.

*Vein color*.—Same color as leaf center on early season top and bottom margins, and nearest RHS 145A in the center on top and bottom; mid season and later nearest RHS 145B on top and bottom center and nearest RHS 144B on top and bottom margins.

*Petioles*.—Semi-conduplicate to concavo-convex, glabrous, slightly glaucous, arching; 38 to 42 cm long and about 1.3 cm wide measured at 3 cm above soil line.

*Petiole color*.—Both edges of petiole nearest RHS N144A in the distal region, nearest RHS 144A in the center distal region; and proximal and middle center nearest RHS N144C and margin nearest RHS N144A with a slight glaucous surface.

Flower description:

*Buds*.—Clavate with bluntly acute to rounded apex and longer thin base; one day prior to opening nearest RHS 91D near base and lighter (more white) than RHS 91D at middle and green apex nearest RHS 144A; about 5.0 cm long, and 1.5 cm wide at the broadest portion.

*Flowers*.—28 to 36 per scape; each subtended by bract; funnelform; about 5.0 cm wide and 6.5 cm long, (distal flowers slightly smaller); remain open for a normal period, usually one to two days on or cut from plant; scapes remain effective from mid June into early July in Zeeland, Mich.; no detectable fragrance.

*Tepals*.—Two sets of three fused at the basal two thirds; acute apex; margins entire; glabrous, approximately 6.5 cm long and 2.0 cm wide; inner tepal color nearest RHS 91D on the center stripe of about 6 mm wide and white on the outer margins; outer tepal color lighter than RHS 91D throughout the tepal margin to center with the basal 1 cm nearest RHS 91D; veins not prominent, same color as surrounding tissue.

*Pedicel*.—Rounded, slightly curved, glaucous, glabrous; about 1.2 cm long, 3 mm diameter; between RHS 138C and RHS 138 B with slight lavender undertones.

*Peduncle*.—Cylindrical, glaucous, glabrous, unbranched; usually one per division, slightly arching, about 6 mm diameter at base, about 60 cm tall; nearest RHS 139C.

*Gynoecium*.—Single; Style: about 7.0 cm long, 1 mm diameter, curled upward at distal 1.0 cm; lighter than RHS 142 in the proximal half and whiter than RHS 155D in the distal half.

*Stigma*.—Rounded, 1 mm to 2 mm in diameter, lighter than RHS 155D.

*Androecium*.—Filaments: six, about 1.0 mm in diameter and 7.5 cm long, shorter than gynoecium; curving upward the last 1.5 cm; lighter than RHS 142 in the proximal half and whiter than RHS 155D in the distal half.

*Anthers*.—Oblong; attached midpoint lengthwise; dehiscing along the center longitudinal axis; about 5 mm long and 2 mm wide, between RHS 187A and RHS 187B.

*Pollen*.—Elliptical, less than 0.1 mm long, nearest RHS 17B.

*Bracts*.—Subtending each flower, sessile, lanceolate, entire, glaucous, glabrous, widest at base and tapering to acute apex; protruding upward about 80 degree angle away from scape at time of flower opening; lowest up to 6.0 cm long and 1.25 cm wide before first flower, progressively decreasing in both length and width; drying as flowers open.

*Bract color*.—Center portion on top and bottom surfaces lighter than RHS 145D with outer portion nearest RHS 139C and a thin margin about 1 mm wide of nearest RHS 139D.

Fruit: Has not been observed.

Seeds: Have not been observed.

Disease resistance: Disease or pest resistance beyond that common to *Hostas* has not been observed. The plant grows best with light fertilizer, plenty of moisture and adequate drainage, but is able to tolerate some flooding and drought when mature. Hardiness at least from USDA zone 3 through 9, and other disease resistance is typical of that of other *Hostas*.

I claim:

1. A new and distinct ornamental *Hosta* plant named 'Goodness Gracious' as herein described and illustrated, with ovate leaves with wide yellow margins and dark green centers, light lavender flowers, suitable as a potted plant, for the garden, and for cut flower or leaf arrangements.

* * * * *